(12) United States Patent
Yang et al.

(10) Patent No.: US 11,426,114 B2
(45) Date of Patent: Aug. 30, 2022

(54) METHOD AND SYSTEM FOR MEASURING SPASTICITY

(71) Applicant: METAL INDUSTRIES RESEARCH & DEVELOPMENT CENTRE, Kaohsiung (TW)

(72) Inventors: Sheng-Hong Yang, Kaohsiung (TW); Bo-Wei Pan, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 886 days.

(21) Appl. No.: 16/228,773

(22) Filed: Dec. 21, 2018

(65) Prior Publication Data

US 2020/0196902 A1 Jun. 25, 2020

(51) Int. Cl.
*A61B 5/389* (2021.01)
*G06T 7/00* (2017.01)
*A61B 5/00* (2006.01)
*A61B 5/11* (2006.01)

(52) U.S. Cl.
CPC ............ *A61B 5/389* (2021.01); *A61B 5/1114* (2013.01); *A61B 5/7253* (2013.01); *A61B 5/7264* (2013.01); *G06T 7/0012* (2013.01); *A61B 2562/0219* (2013.01); *A61B 2562/0247* (2013.01); *G06T 2207/20084* (2013.01); *G06T 2207/30004* (2013.01)

(58) Field of Classification Search
CPC ..... A61B 5/389; A61B 5/1114; A61B 5/7253; A61B 5/7264; A61B 2562/0219; A61B 2562/0247; G06T 7/0012; G06T 2207/20084; G06T 2207/30004
See application file for complete search history.

(56) References Cited

U.S. PATENT DOCUMENTS

2007/0091091 A1\* 4/2007 Gardiner ............... G06T 11/206 345/440
2015/0019139 A1 1/2015 Liljeryd et al.
2016/0345842 A1\* 12/2016 Liljeryd ............... A61B 5/7267
2017/0293805 A1\* 10/2017 Kontschieder ......... G16H 20/30
2018/0020951 A1\* 1/2018 Kaifosh .................. G06F 3/014 607/48

FOREIGN PATENT DOCUMENTS

WO 2018022597 A1 2/2018

\* cited by examiner

*Primary Examiner* — Daniel L Cerioni
(74) *Attorney, Agent, or Firm* — CKC & Partners Co., LLC

(57) ABSTRACT

A method for measuring spasticity is provided and includes: obtaining sensing signals corresponding to a limb movement through at least one sensor during a period of time; transforming the sensing signals into a two-dimensional image; and inputting the two-dimensional image into a convolutional neural network to output a spasticity determination result.

6 Claims, 6 Drawing Sheets

METHOD AND SYSTEM FOR MEASURING SPASTICITY

BACKGROUND

Field of Invention

The present invention relates to a method for measuring spasticity. More particularly, the present invention relates to the method for measuring spasticity by using a convolutional neural network.

Description of Related Art

With the advancement of medical technology, the success rate of disease treatment has increased, resulting in longer life expectancy. However, some patients may not fully recover after treatment. For example, if limb hemiplegia occurs after patients with brain or spinal cord injury are treated, then they need some rehabilitation processes for fulling recovery. In an aging society, the need for medical care during the rehabilitation process has also increased. During the rehabilitation of patients with hemiplegia due to stroke, cerebral palsy, Parkinson's disease or spinal cord injury, they will experience abnormal muscle tension, leading to clinical symptoms such as muscle spasticity and stiffness. Therefore, a doctor has to apply force to the limb of the patents, and refers to a relevant scale to diagnose the abnormal muscle tension based on subjective experience. The diagnosis results of different doctors may be different, which is difficult to call objective. In addition, a conventional velocity muscle tester is mainly used for athletes' testing, which is bulky and expensive; and the conventional micro muscle force sensor can only be used for simple muscle strength test instead of measuring muscle abnormality level, and thus the doctors or health care provider cannot effectively diagnose the condition of the patent and provide immediate treatments. In view of this, it is necessary to improve the shortcomings of the above prior art to meet the actual needs and improve its practicability.

SUMMARY

Embodiments of the present invention provide a method for measuring spasticity. The method includes: obtaining, by a at least one sensor, at least one sensing signal corresponding to a limb movement during a time period; transforming the at least one sensing signal into a two-dimensional image; and inputting the two-dimensional image into a convolutional neural network to output a spasticity determination result.

In some embodiments, the at least one sensor includes an inertial sensor, an electromyography sensor, a pressure sensor, or a combination thereof.

In some embodiments, the at least one sensing signal includes acceleration signals and an electromyography signal. The step of transforming the at least one sensing signal into the two-dimensional image includes: arranging values of the acceleration signals and the electromyography signal in a same two-dimensional image.

In some embodiments, the step of transforming the at least one sensing signal into the two-dimensional image includes: generating the two-dimensional image according to a following equation (1).

$$I_{i,j} = \text{diff}(a_{1,i}, a_{2,j}) \tag{1}$$

$I_{i,j}$ denotes a grey level at $i^{th}$ column and $j^{th}$ raw of the two-dimensional image. $a_{1,i}$ denotes a value of one of the acceleration signals at a time point i. $a_{2,j}$ denotes a value or another one of the acceleration signals at a time point j. diff ( ) is a difference function for the two values.

In some embodiments, the difference function diff( ) is written as a following equation (2) where $c_1$, $c_2$ are constants $$\text{diff}(a_{1,i}, a_{2,j}) = c_1 \times |a_{1,i} - a_{2,j}| + c_2 \times |(a_{1,i+1} - a_{1,i-1}) - (a_{2,j+1} - a_{2,j-1})| \tag{2}$$

From another aspect, embodiments of the present invention provide a system for measuring spasticity. The system includes at least one sensor and a computation circuit. The at least one sensor obtains at least one sensing signal corresponding to a limb movement during a time period. The computation circuit is coupled to the at least one sensor for transforming the at least one sensing signal into a two-dimensional image, and inputting the two-dimensional image into a convolutional neural network to output a spasticity determination result.

In some embodiments, the computation circuit arranges values of the acceleration signals and the electromyography signal in a same two-dimensional image.

In some embodiments, the computation circuit forms the two-dimensional image according to the equation (1).

In the aforementioned method and system, features of the sensing data are automatically extracted by the convolutional neural network.

BRIEF DESCRIPTION OF THE DRAWINGS

The invention can be more fully understood by reading the following detailed description of the embodiment, with reference made to the accompanying drawings as follows.

DETAILED DESCRIPTION

The using of "first", "second", "third", etc. in the specification should be understood for identifying units or data described by the same terminology, but are not referred to particular order or sequence.

In the prior art, medical staff can guide a patient to bend an affected part, such as arm, and give a score according to the muscle reaction of the bended part. Please refer to Table 1 below which shows Ashworth scores or said modified Ashworth scores.

TABLE 1

| Score | Definition |
| --- | --- |
| 1 | No increase in muscle tone (Normal). |
| 2 | Slight increase in muscle tone (manifested by a catch and release or by minimal resistance at the end of the range of motion (ROM) when the affected part(s) is moved in flexion or extension). |

TABLE 1-continued

Score Definition

3  Slight increase in muscle tone (manifested by a catch, followed by minimal resistance throughout the remainder (less than half) of the ROM.
4  More marked increase in muscle tone through most of the ROM, but affected part(s) easily moved.
5  Considerable increase in muscle tone, passive movement difficult.
6  Affected part(s) rigid in flexion or extension.

A system and a method for measuring spasticity are provided in which data obtained from sensors are used to objectively output a spasticity determination result (e.g. the Score of Table 1).

Figure 1:
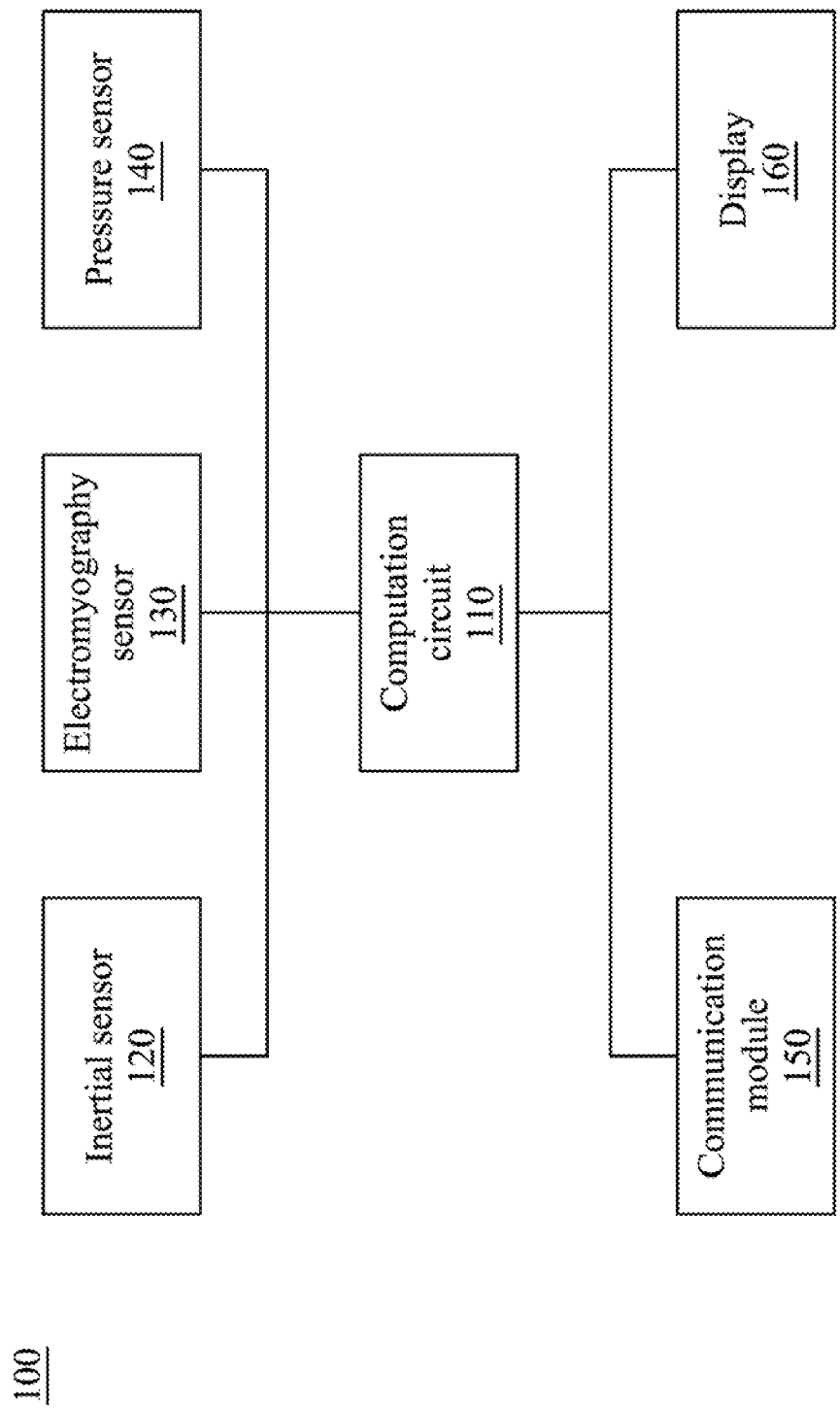
FIG. 1 is a schematic diagram of a system for measuring spasticity in accordance with an embodiment.

FIG. 1 is a schematic diagram of a system for measuring spasticity in accordance with an embodiment. Referring to FIG. 1, a system 100 includes a computation circuit 110, an inertial sensor 120, an electromyography sensor 130, a pressure sensor 140, a communication module 150, and a display 160. The computation circuit 110 may be a central processing unit, a microprocessor, a microcontroller, a digital signal processor, an image processing chip, an application-specific integrated circuit, etc. The inertial sensor 120 is, for example, a 9-axis sensor including a 3-axis acceleration sensor, a gyroscope and a magnetometer. The 3-axis acceleration sensor can sense accelerations along X, Y, and Z axes. The gyroscope can sense angular velocity. The magnetometer can sense the orientation and intensity of a magnetic field, and then an angle can be obtained accordingly. The electromyography sensor 130 is configured to measure electromyography (EMG) signals. The pressure sensor 140 is configured to measure pressures applied on the sensor. The communication module 150 may be a wire or wireless communication module such as a wireless fidelity (WiFi), near field communication (NFC) or Bluetooth module. The display 160 may be a liquid crystal display, organic light emitting diode (OLED) display or any suitable display for displaying any suitable information such as measured resistance, spasticity determination result, etc.

Figure 2A:
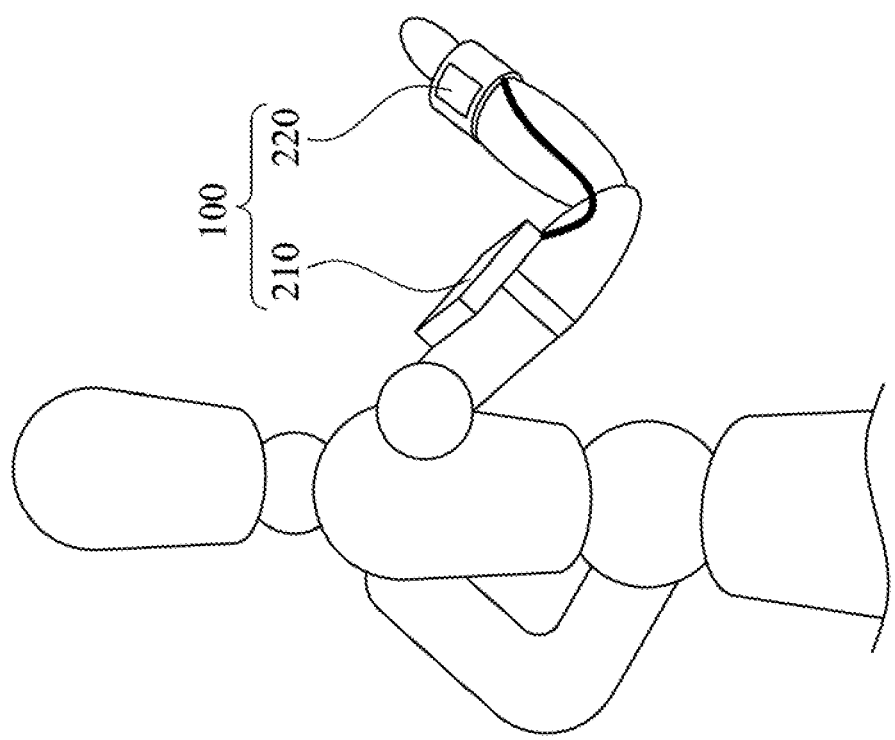
FIG. 2A and FIG. 2B are schematic diagrams of the system for measuring spasticity disposed on a limb in accordance with some embodiments.
Figure 2B:
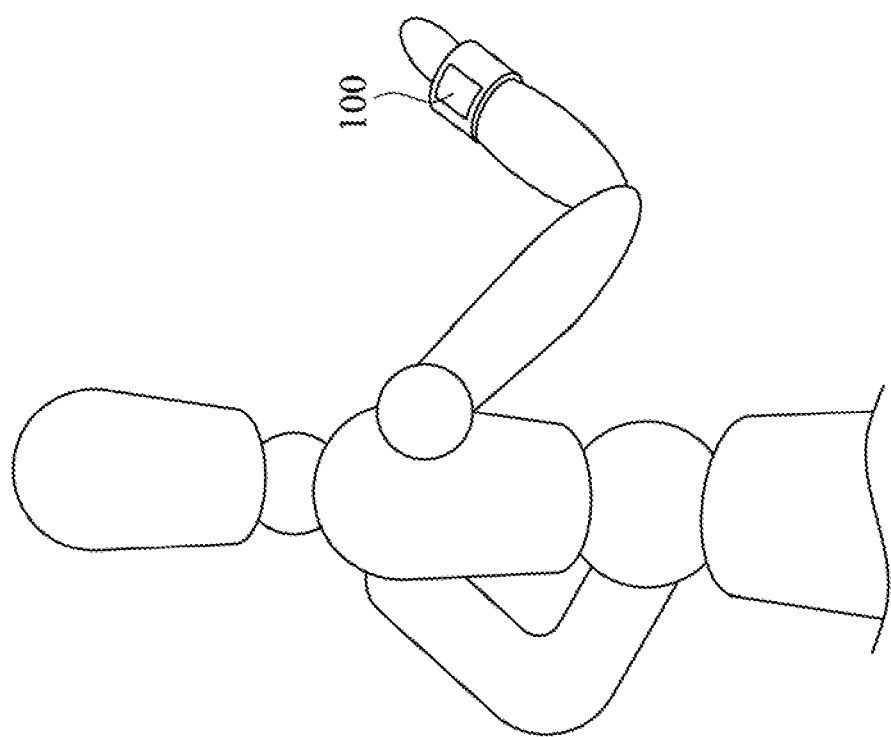

FIG. 2A and FIG. 2B are schematic diagrams of the system for measuring spasticity disposed on a limb in accordance with some embodiments. In the embodiment of FIG. 2A, the system 100 includes two devices 210 and 220. The inertial sensor 120 is disposed on both of the devices 210 and 220. The electromyography sensor 130, the pressure sensor 140, and the computation circuit 110 can be disposed on any one of the devices 210 and 220. When medical staff guides the patient to bend his arm, the sensor will obtains sensing signals corresponding to this limb movement during a time period.

In the embodiment of FIG. 2B, the system 100 includes only one device having all of the components of FIG. 1. That is, only one inertial sensor 120 is disposed in this system 100. The number of devices included in the system 100 is not limited in the invention. In addition, the arrangement of the components among the devices and the number of each sensor are not limited in the invention. The system 100 is disposed on an arm in the embodiments of FIG. 2A and FIG. 2B, but it may be disposed on a foot or any suitable part of human body in other embodiments.

In the embodiment, the data obtained by the sensors is inputted into a convolutional neural network which is typically used to process a two-dimensional image. Therefore, the one-dimensional sensing signals are transformed into the two-dimensional image that will be described in detail below.

Figure 3:
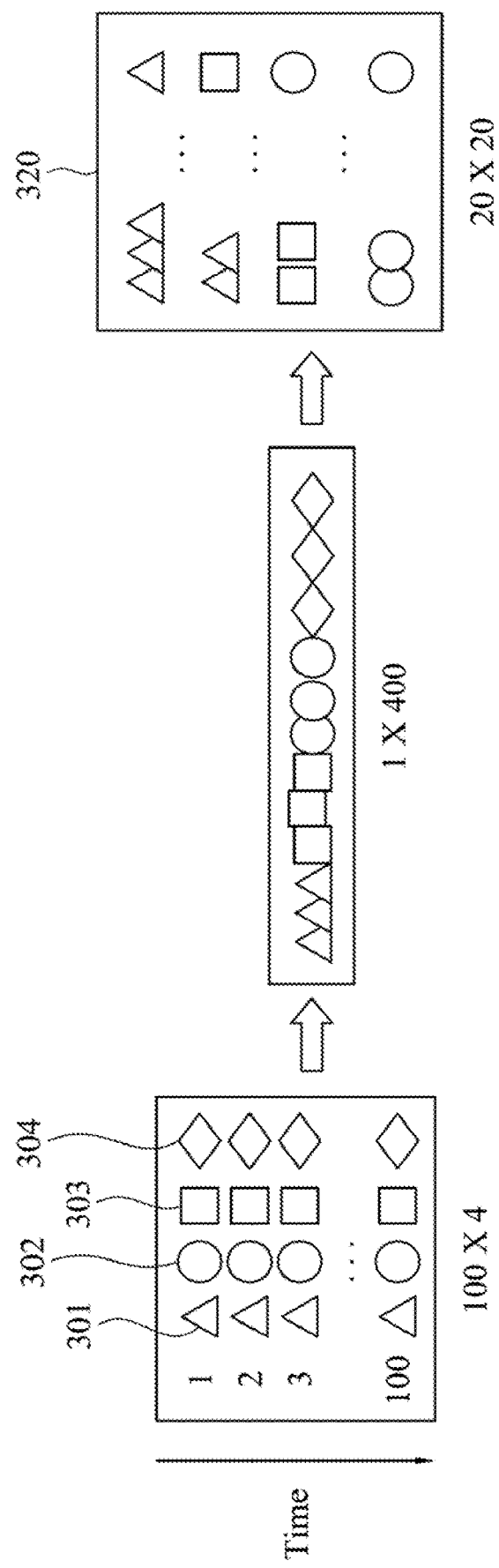
FIG. 3 is a schematic diagram of transforming sensing signals in accordance with an embodiment.

FIG. 3 is a schematic diagram of transforming sensing signals in accordance with an embodiment. Referring to FIG. 1 and FIG. 3, the computation circuit 110 obtains multiple sensing signals from the inertial sensor 120, the electromyography sensor 130, and the pressure sensor 140. Assume there are 100 sample points during a time period, then a total of 100*n sensing values are obtained from n sensors where n is a positive integer. There are four sensing signals 301-304 in FIG. 3 where the sensing signal 301 is an X-axis acceleration signal, the sensing signal 302 is a Y-axis acceleration signal, the sensing signal 303 is a Z-axis acceleration signal, and the sensing signal 304 is an electromyography signal. Values of the signals with the identical types are illustrated as the same symbol. For example, the triangles represent values of the X-axis acceleration signal, and so on. Note that each of the sensing signals 301-304 has 100 sample points, and therefore there are a total of 4*100 sensing values. In some embodiments, a pre-process such as de-noise, normalization, etc. is performed on these sensing values where a Kalman filter is used for de-noise, but the invention is not limited thereto. These 400 sensing values are first arranged in sequence, and then arranged in the same two-dimensional image 320 with size 20*20. In some embodiments, the sensing signal 301 is arranged from the first row of the two-dimensional image 320, and then the other sensing signals 302-304 are arranged row by row. However, the sensing signal 301 may be arranged from the first column of the two-dimensional image 320, which is not limited in the invention.

Figure 4:
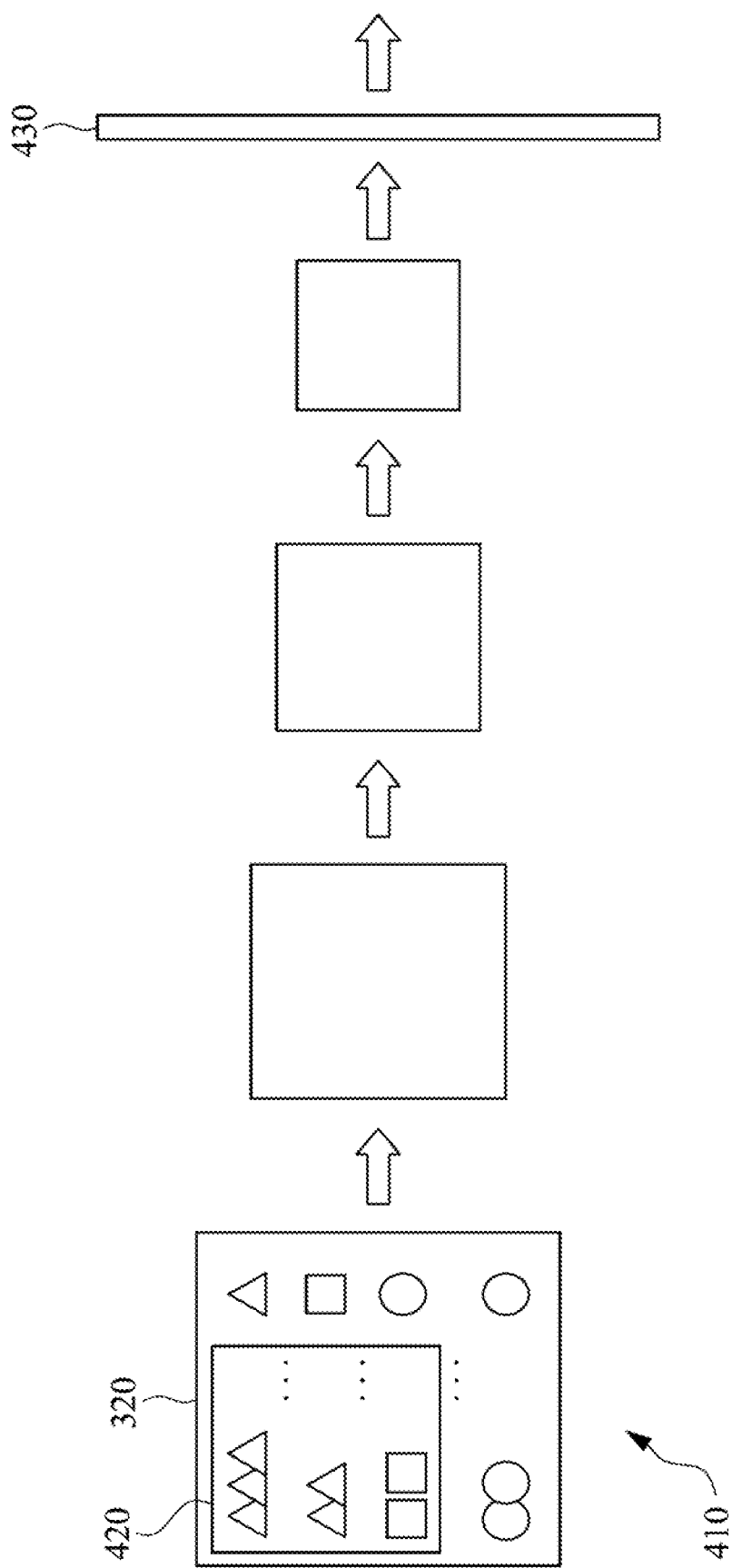
FIG. 4 is a schematic diagram of inputting a two-dimensional image into a convolutional neural network in accordance with an embodiment.

FIG. 4 is a schematic diagram of inputting a two-dimensional image into a convolutional neural network in accordance with an embodiment. Referring to FIG. 4, the two-dimensional image 320 is inputted into a convolutional neural network 410 (in a training phase or a test phase). The convolutional neural network 410 may include convolutional layers, pooling layers, transfer functions and fully connected layers. The transfer function, such as Rectified linear unit (ReLU), is in neurons of the convolutional layers, but other transfer functions may adopted in other embodiments. People skilled in the art should be able to understand the operation of the convolutional neural network, and therefore the detail will not be described. The depth of the convolutional neural network 410 and the number of the pooling layers are limited in the invention. Note that a filter may cover a range 420 having different types of sensing signal. The end of the convolutional neural network 410 is a fully connected layer 430 for outputting a vector with size of 1*6. The vector is normalized by a softmax function, and the normalized values represent the spasticity determination result such as the scores in Table 1. In the training phase, the output of the convolutional neural network is a vector determined by medical staff. If the spasticity determination result is score "1", then the vector is [1,0,0,0,0,0]. On the other hand, if the outputted vector is [0.513, 0.667, 0.602, 0.521, 0.379, 0.187] in the test phase where the maximum number is "0.667", it indicates the score "2". The output of the convolutional neural network 410 is the vector with size of 1*6 in the embodiment, but it may be a vector which has longer or shorter length in other embodiments. The meaning of each value in the vector is not limited in the invention, either.

The acceleration signals and the electromyography signal are transformed into the two-dimensional image 320 in the aforementioned embodiment, but angular velocity signals, orientation signals of magnetic field may be included in the image. Alternatively, the sensing signals obtained by another inertial sensor may also be included in the image. In other words, the sensing signals obtained by the sensors of FIG. 1 may be arranged as any combination as the two-dimensional image 320, which is not limited in the invention.

All sensing signals are arranged in the same two-dimensional image in the aforementioned embodiments, but a symmetric matrix is generated according to one or more sensing signal so as to transform the one-dimension sensing signals into two-dimensional images in other embodiments. For example, take the acceleration signals as an example, a two-dimensional image is generated according to the following equation (1).

$$I_{i,j} = \text{diff}(a_{1,i}, a_{2,j}) \tag{1}$$

$I_{i,j}$ denotes a grey level at $i^{th}$ column and $j^{th}$ raw of the two-dimensional image. $a_{1,i}$ denotes a value of one of the acceleration signals at a time point i. $a_{2,i}$ denotes a value or another one of the acceleration signals at a time point j. For example, $a_{1,i}$ may be the X-axis acceleration signal, and $a_{2,i}$ may be the Y-axis acceleration signal. diff( ) is a difference function for the two values that may be written as the following equation (2).

$$\text{diff}(a_{1,i}, a_{2,j}) = c_1 \times |a_{1,i} - a_{2,j}| + c_2 \times |(a_{1,i+1} - a_{1,i-1}) - (a_{2,j+1} - a_{2,j-1})| \tag{2}$$

$c_1$, $c_2$ are constants which may be determined through experiments. Note that $|a_{1,i} - a_{2,j}|$ of the equation (2) is used to represent the difference between two accelerations, and $|(a_{1,i+1} - a_{1,i-1}) - (a_{2,j+1} - a_{2,j-1})|$ is the difference between slops of the acceleration signals. Therefore, the equation (2) can effectively distinguish the two signals. For example, $a_{1,i}$ may be equal to $a_{2,j}$, but $a_{1,i}$ is in an increasing trend and $a_{2,j}$ is in a decreasing trend. In this case, diff($a_{1,i}, a_{2,j}$) of equation (2) will not be 0 for indicating that the two signals are different from the each other. Also note that the equation (2) may be applied to any two of the acceleration signals, and thus 3 two-dimensional images may be generated according to the X, Y, and Z acceleration signals. In addition, a two-dimensional image may be generated according to the following equation (3).

$$I_{i,j} = \text{diff}(e_i, e_j) \tag{3}$$

$e_i$, $e_j$ denotes values of the electromyography signal at time points i and j respectively. Accordingly, four two-dimensional images are generated in the embodiment of FIG. 3. From another aspect, the 4 generated two-dimensional images are different channels of single one two-dimensional image, similar to red, green, and blue channels of a color image. Next, the two-dimensional image with four channels is inputted to the convolutional neural network 410. As a result, the filers in the convolutional layer can process three acceleration signals and one electromyography signal simultaneously. In some embodiments, the acceleration signals, angular velocity signals, orientation signals, or combinations thereof may be applied to the equation (1) or (2) to generate more two-dimensional images, which is not limited in the invention. In general, the convolutional neural network can automatically extract features from the images without experts to determine the features. In the embodiment, the acceleration signals, the angular velocity signal, the electromyography signal, etc. are transformed into two-dimensional images, and therefore they can be inputted to the convolutional neural network for the sake of auto feature extraction.

Figure 5:
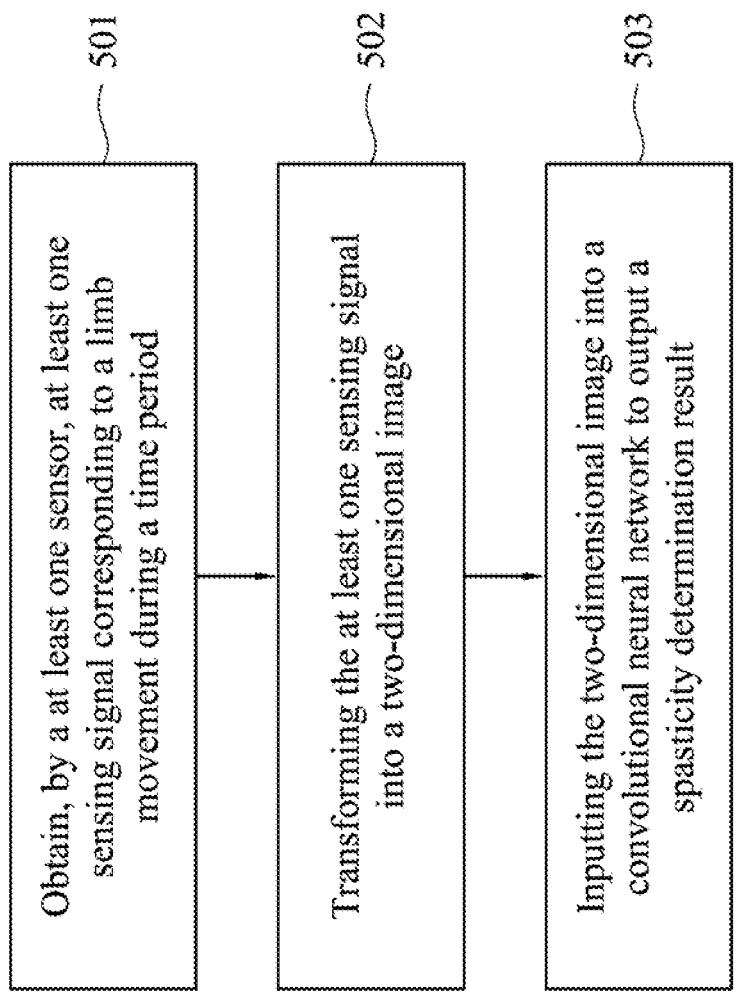
FIG. 5 is a flow chart of a method for measuring spasticity in accordance with an embodiment.

FIG. 5 is a flow chart of a method for measuring spasticity in accordance with an embodiment. In step 501, sensing signals corresponding to a limb movement during a time period are obtained. In step 502, the sensing signals are transformed into a two-dimensional image. In step 503, the two-dimensional image is inputted into a convolutional neural network to output a spasticity determination result. However, all the steps in FIG. 5 have been described in detail above, and therefore they will not be repeated. Note that the steps in FIG. 5 can be implemented as program codes or circuits, and the disclosure is not limited thereto. In addition, the method in FIG. 5 can be performed with the aforementioned embodiments, or can be performed independently. In other words, other steps may be inserted between the steps of the FIG. 5.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for measuring spasticity, comprising:
    obtaining, by a at least one sensor, at least one sensing signal corresponding to a limb movement during a time period;
    transforming the at least one sensing signal into a two-dimensional image; and
    inputting the two-dimensional image into a convolutional neural network to output a spasticity determination result,
    wherein the at least one sensor comprises an inertial sensor, the at least one sensing signal comprises a plurality of acceleration signals, and the step of transforming the at least one sensing signal into the two-dimensional image comprises:
    generating the two-dimensional image according to a following equation (1):

$$I_{i,j} = \text{diff}(a_{1,i}, a_{2,j}) \tag{1}$$

wherein $I_{i,j}$ denotes a grey level at $i^{th}$ column and $j^{th}$ raw of the two-dimensional image, $a_{1,i}$ denotes a value of one of the acceleration signals at a time point i, $a_{2,j}$ denotes a value or another one of the acceleration signals at a time point j, and diff( ) is a difference function for two values.

2. The method of claim 1, wherein the at least one sensor further comprises an electromyography sensor, or a pressure sensor.

3. The method of claim 1, wherein the difference function diff( ) is written as a following equation (2):

$$\text{diff}(a_{1,i}, a_{2,j}) = c_1 \times |a_{1,i} - a_{2,j}| + c_2 \times |(a_{1,i+1} - a_{1,i-1}) - (a_{2,j+1} - a_{2,j-1})| \tag{2}$$

wherein $c_1$, $c_2$ are constants.

4. A system for measuring spasticity, comprising:
    at least one sensor, configured to obtain at least one sensing signal corresponding to a limb movement during a time period; and
    a computation circuit coupled to the at least one sensor and configured to transform the at least one sensing signal into a two-dimensional image, and input the two-dimensional image into a convolutional neural network to output a spasticity determination result, wherein the at least one sensor comprises an inertial sensor, and the at least one sensing signal comprises a plurality of acceleration signals, wherein the computation circuit is configured to generate the two-dimensional image according to a following equation (1):

$$I_{i,j} = \text{diff}(a_{1,i}, a_{2,j}) \quad (1)$$

wherein $I_{i,j}$ denotes a grey level at $i^{th}$ column and $j^{th}$ raw of the two-dimensional image, $a_{1,i}$ denotes a value of one of the acceleration signals at a time point i, $a_{2,j}$ denotes a value or another one of the acceleration signals at a time point j, diff( ) is a difference function for two values.

5. The system of claim 4, wherein the at least one sensor further comprises an electromyography sensor, or a pressure sensor.

6. The system of claim 4, wherein the difference function diff( ) is written as a following equation (2):

$$\text{diff}(a_{1,i}, a_{2,j}) = c_1 \times |a_{1,i} - a_{2,j}| + c_2 \times |(a_{1,i+1} - a_{1,i-1}) - (a_{2,j+1} - a_{2,j-1})| \quad (2)$$

wherein $c_1$, $c_2$ are constants.

\* \* \* \* \*